US009285327B2

(12) United States Patent
Ying

(10) Patent No.: US 9,285,327 B2
(45) Date of Patent: Mar. 15, 2016

(54) ADJUSTABLE PHOTON DETECTION SYSTEMS FOR MULTI-SLICE X-RAY COMPUTED TOMOGRAPHY SYSTEMS

(71) Applicant: Zhengrong Ying, Belmont, MA (US)

(72) Inventor: Zhengrong Ying, Belmont, MA (US)

( * ) Notice: Subject to any disclaimer, the term of this patent is extended or adjusted under 35 U.S.C. 154(b) by 435 days.

(21) Appl. No.: 13/760,127

(22) Filed: Feb. 6, 2013

(65) Prior Publication Data

US 2014/0219415 A1      Aug. 7, 2014

(51) Int. Cl.
*A61B 6/03*      (2006.01)
*G01N 23/04*    (2006.01)
*G01T 1/29*      (2006.01)
*A61B 6/00*      (2006.01)

(52) U.S. Cl.
CPC ............... *G01N 23/046* (2013.01); *A61B 6/032* (2013.01); *A61B 6/4233* (2013.01); *A61B 6/4291* (2013.01); *G01T 1/2985* (2013.01); *A61B 6/4085* (2013.01); *A61B 6/5258* (2013.01); *A61B 6/585* (2013.01); *G01N 2223/419* (2013.01)

(58) Field of Classification Search
CPC .... A61B 6/5282; A61B 6/032; A61B 6/4233; A61B 6/4266; A61B 6/06; A61B 6/4291
See application file for complete search history.

(56) References Cited

U.S. PATENT DOCUMENTS

| | | | |
|---|---|---|---|
| 4,352,020 A | 9/1982 | Horiba | |
| 6,081,576 A | 6/2000 | Schanen | |
| 6,198,791 B1 | 3/2001 | He | |
| 6,235,993 B1 | 5/2001 | Johnston | |
| 6,522,715 B2 | 2/2003 | Hoffman | |
| 6,778,637 B2 | 8/2004 | Luhta | |
| 6,982,423 B2 | 1/2006 | Elgali | |
| 7,177,387 B2 | 2/2007 | Yasunaga | |
| 7,582,879 B2 | 9/2009 | Abenaim | |
| 7,606,346 B2 | 10/2009 | Tkaczyk | |
| 9,078,569 B2* | 7/2015 | Ying | A61B 6/032 |
| 9,222,904 B2* | 12/2015 | Harrison | G01N 25/72 |
| 2006/0233298 A1* | 10/2006 | Igarashi | G21K 1/025 378/19 |
| 2012/0328076 A1* | 12/2012 | Ikhlef | 378/62 |

OTHER PUBLICATIONS

Authors: Kak and Slaney, book title: Principles of Computerized Tomographic Imaging, published by IEEE Press in Jan. 1989, Chapter 3.4.1, pp. 77-86.
Authors: Kachelriess, Schaller, and Kalender, article title: Advanced single-slice rebinning in cone-beam spiral CT, journal title:Medical Physics, vol. 27, No. 4, pp. 754-772, Apr. 2000.

* cited by examiner

Primary Examiner — Hoon Song

(57) ABSTRACT

An Adjustable Photon Detection System (APDS) for multi-slice X-ray CT systems and a multi-slice X-ray CT system using the APDS are disclosed; wherein the APDS can be adjusted to be aligned to different X-ray source positions; wherein the multi-slice X-ray CT system comprises one or more X-ray sources, and one or more APDS; wherein the multi-slice X-ray CT system may also include a detector position calculator for calculating effective detector positions and a detector position corrector for correcting projection data using calculated effective detector positions.

17 Claims, 7 Drawing Sheets

ADJUSTABLE PHOTON DETECTION SYSTEMS FOR MULTI-SLICE X-RAY COMPUTED TOMOGRAPHY SYSTEMS

RELATED APPLICATIONS

This patent application is related to the following pending U.S. applications and/or issued U.S. patents, the contents of which are incorporated herein in their entirety by reference:

"Configurable data measurement and acquisition systems for multi-slice x-ray computed tomography systems," invented by Zhengrong Ying, U.S. application Ser. No. 13/589,245, filed on Aug. 20, 2012.

FIELD OF THE DISCLOSURE

The present disclosure relates to multi-slice X-ray Computed Tomography (CT) systems.

BACKGROUND

In X-ray CT systems, X-rays are used to image internal structures and features of a region of a subject or an object. The terms "subject" and "object" shall include anything capable of being imaged. The imaging is performed by an X-ray CT system, which images internal structures and features of a plurality of thin planar slices or a 3D volume of a region of an object using X-rays. For medical applications, the imaging objects include human bodies.

An X-ray CT system generally comprises an X-ray source that provides a cone-shaped X-ray beam and an array of closely spaced X-ray detectors that face the X-ray source. The X-ray source and the array of detectors are mounted in a gantry so that a patient being imaged with the CT system, generally lying on an appropriate support couch, can be positioned within the gantry between the X-ray source and the array of detectors. The gantry and the couch are moveable relative to each other so that the X-ray source and the detector array can be positioned axially at desired locations along the patient's body.

The gantry comprises a stationary structure referred to as a stator and a rotary element referred to as a rotor, which is mounted to the stator so that the rotor is rotatable about the axial direction. In third generation CT systems, the X-ray source and the array of detectors are mounted on the rotor. Angular positions of the rotor about the axial direction are controllable so that the X-ray source can be positioned at desired angles, referred to as view angles, around a patient's body.

To image a slice in a region of a patient's body, the X-ray source is positioned at an axial position of the slice and the X-ray source is rotated around the slice to illuminate the slice with X-rays from a plurality of different view angles. At each view angle, detectors in the array of detectors generate signals responsive to the intensity of X-rays from the source that pass through the slice. The signals are processed to determine the amounts, by which X-rays from the X-ray source are attenuated over various path lengths through the slice that the X-rays traverse, in passing though the slice from the X-ray source to the detectors. The amounts, by which the X-rays are attenuated, are used to determine the X-ray absorption coefficients of materials in the slice as a function of position in the slice. The absorption coefficients are used to generate an image of the slice and identify compositions and densities of tissues in the slice.

The X-ray detectors comprised in a detector array of CT system are generally packaged in a plurality of modules, hereinafter referred to as detector modules, each of which comprises a plurality of X-ray detector elements. Most modern CT systems are multi-slice CT systems designed to simultaneously image a plurality of slices of a patient. The X-ray detector elements in each detector module of a multi-slice CT scanner are arranged in a matrix of rows and columns. The X-ray detector matrices of any two CT detector modules in a CT system are substantially identical and comprise a same number of rows of detector elements and a same number of columns of detector elements. The modules are positioned one adjacent to and contiguous with the other in a closely packed array with their rows of detectors aligned end to end so that the X-ray detector elements form a plurality of long parallel rows of X-ray detector elements.

A multi-slice X-ray CT system is usually named or featured by the maximum number of slices that it can simultaneously image, for example, an 8-slice CT system means that it can simultaneously image at most 8 slices; a 16-slice CT system can simultaneously image at most 16 slices.

The X-ray detector elements in each long row of the detector array lie on an arc of a circle having its center located at a focal point of the CT system's X-ray source, and the design of these detector elements and the detector modules is specifically determined by the radius of the circle, which is hereinafter referred to as focusing distance. The design of X-ray detector modules placed on the arc of one focusing distance of one CT system cannot therefore be used on another CT system of a different focusing distance.

X-ray detector arrays typically include a collimator having a plurality of anti-scatter plates for collimating x-ray beams received at each detector element; a scintillator for converting x-rays to light energy adjacent the collimator, and a photodiode for receiving the light energy from the coupled scintillator and producing electric charges therefrom. The anti-scatter plates of a collimator are bonded with the elements of the scintillator arrays to very tight and exact tolerances. This bonding of the plurality of elements of the scintillator array and the anti-scatter plates of the collimator can be a time consuming and a labor intensive process.

Electronic components for processing analog signals from the X-ray detector elements in a CT detector module are usually located at positions removed from the detector module. Each detector element in a detector module is connected to the module's electronic processing components via a cable over which analog signals from the detector elements are transmitted to the processing electronics. Because the electric charges produced by the photodiodes are extremely small, the cables carrying these small charges are very susceptible to interferences, resulting in artifacts in reconstructed CT images; the longer the cables are, the more interferences they are exposed to.

SUMMARY OF THE DISCLOSURE

In accordance with one embodiment of the present disclosure, an Adjustable Photon Detection System (APDS) for a multi-slice X-ray Computed Tomography (CT) system, wherein said X-ray CT system includes at least one X-ray source, comprises: a plurality of X-ray detector modules for receiving and converting X-ray photons; a support structure for mounting said X-ray detector modules, wherein said detector modules focus on a first position; and, a plurality of anti-scatter plates, placed on top of said detector modules; wherein said anti-scatter plates are aligned to a second position; wherein said second position may be different from said first position.

In accordance with one embodiment of the present disclosure, a multi-slice X-ray Computed Tomography (CT) system for generating CT images for objects to be imaged comprises: a rotatable gantry; an X-ray source mounted on said rotatable gantry for generating X-ray beams to pass through said objects; and an Adjustable Photon Detection System (APDS) mounted on said rotatable gantry to the opposite side of said X-ray source, for receiving said X-ray beams, and for generating a CT data set corresponding to said objects.

In accordance with one embodiment of the present disclosure, a method of and a system for generating CT images comprise: acquiring a CT data set using a multi-slice X-ray CT system comprising an APDS; generating projection data from said CT data set; performing detector position correction on said generated projection data to generate detector position corrected projection data; and, reconstructing CT images using said detector position corrected projection data.

In accordance with one embodiment of the present disclosure, a method of and a system for generating CT images comprise: acquiring a CT data set using a multi-slice X-ray CT system comprising an APDS; generating projection data from said CT data set; calculating effective detector positions; and, reconstructing CT images using said effective detector positions and said generated projection data.

BRIEF DESCRIPTION OF THE DRAWINGS

The drawing figures depict embodiments by way of example, not by way of limitation. In the figures, like reference numerals refer to the same or similar elements.

DETAILED DESCRIPTION OF THE DRAWINGS

Figure 1:
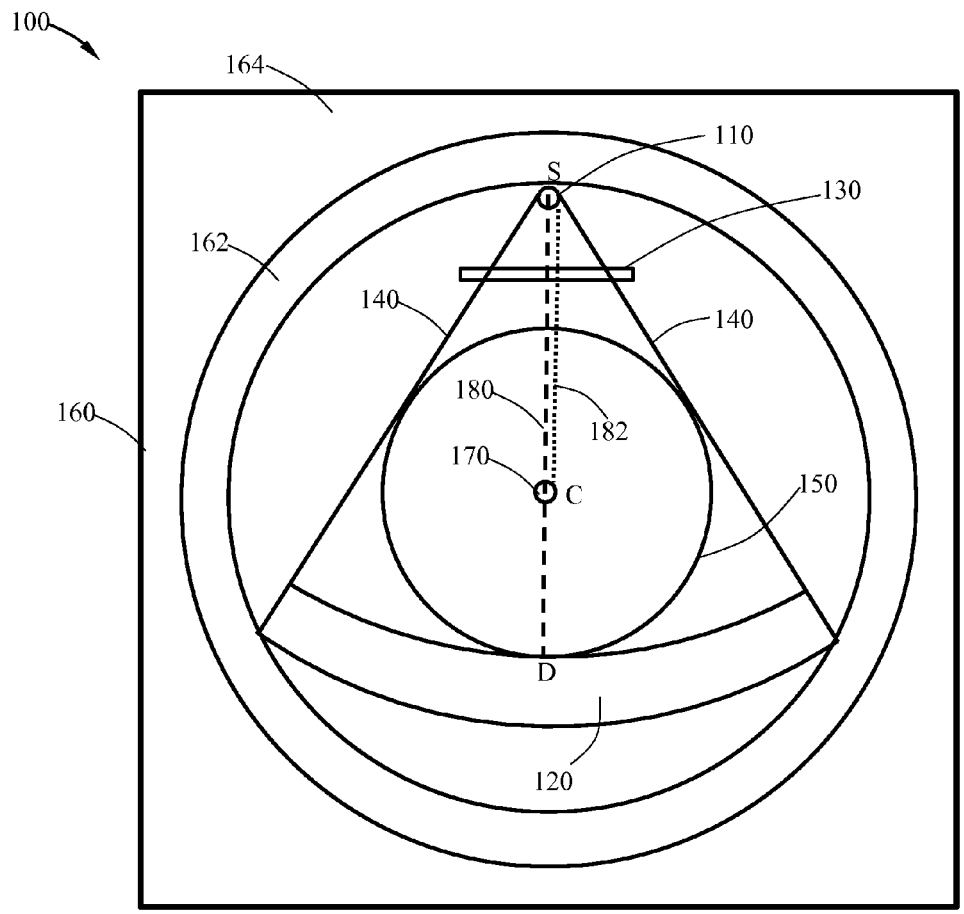
FIG. 1 shows a schematic functional diagram of a prior art multi-slice X-ray CT system.
Figure 1:
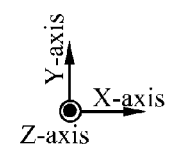

FIG. 1 shows a schematic functional diagram of a prior art multi-slice X-ray CT system 100. A multi-slice CT system typically comprises an X-ray source 110, which generates a cone-shaped X-ray beam 140. The X-ray beam 140 passes through a pre-patient collimator 130, which allows X-ray beam to illuminate only the targeted area and blocks X-ray beam in unwanted area. A patient usually lies down within the scanner's scanning Field Of View (FOV) 150, where the X-ray beam 140 illuminates. The X-ray detector system 120 receives X-ray photons and converts to analog signals that are proportional to X-ray photon energies. The X-ray CT system 100 also comprises a gantry 160, which includes a rotational part 162 and a stationary part 164. The X-ray source 110, the collimator 130 and the detector system 120 are mounted on the rotational part 162 of the gantry 160. The rotational part 162 rotates around the rotation center C 170.

The distance 182 between the focal spot S, which sometimes is interchangeably referred to as X-ray source position, of the X-ray source 110 and the rotation center C, which is interchangeably called iso-center, is hereinafter referred to as $R_{sc}$, and the distance 180 between the focal spot S of the X-ray source 110 and the detector system D is hereinafter referred to as focusing distance $R_{sd}$. Different CT systems may have different $R_{sc}$, $R_{sd}$, or/and scanning FOV.

The direction from the iso-center to the focal spot of the X-ray source is hereinafter referred to as Y-axis, and the direction perpendicular to the imaging plane or the rotation plane is hereinafter referred to as Z-axis, and the direction perpendicular to the Y-axis within the rotation plane is hereinafter referred to as X-axis.

Figure 2:
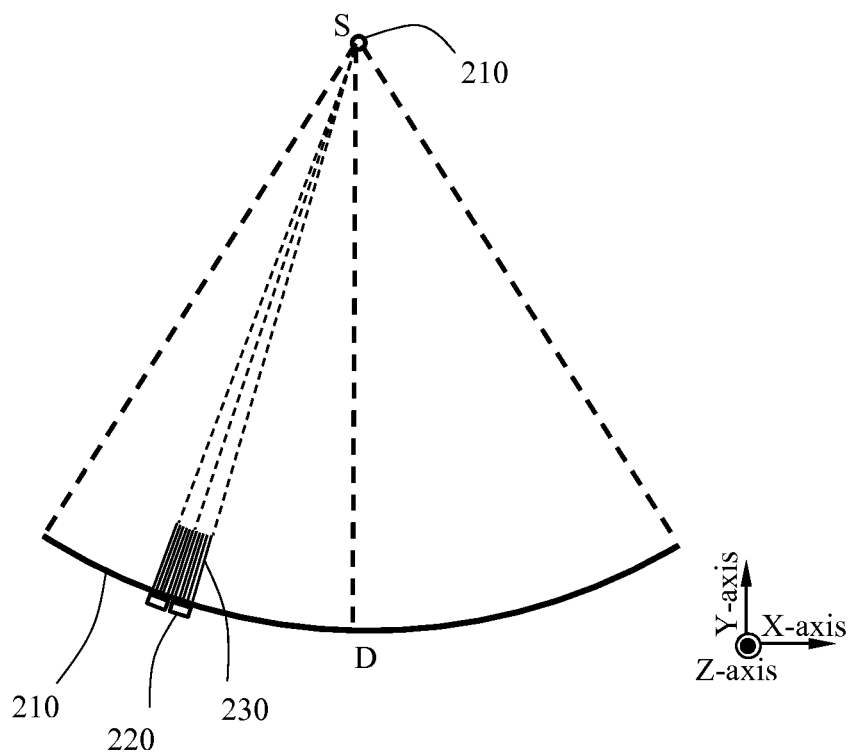
FIG. 2 shows a schematic functional diagram of a prior art CT detector array system.

FIG. 2 shows a schematic functional diagram of a prior art CT detector array system, like the detector array system 120 in the prior art CT system 100 of FIG. 1. The detector array system typically comprises a plurality of detector modules 220 mounted on an arced support structure 210, and anti-scatter plates 230. In a prior art CT system, the center of the arced support structure 210 is at the X-ray source position S 210; the detector modules 220 focus on the X-ray source position S 210; and, the anti-scatter plates 230 are also aligned to X-ray source position S 210.

Figure 3A:
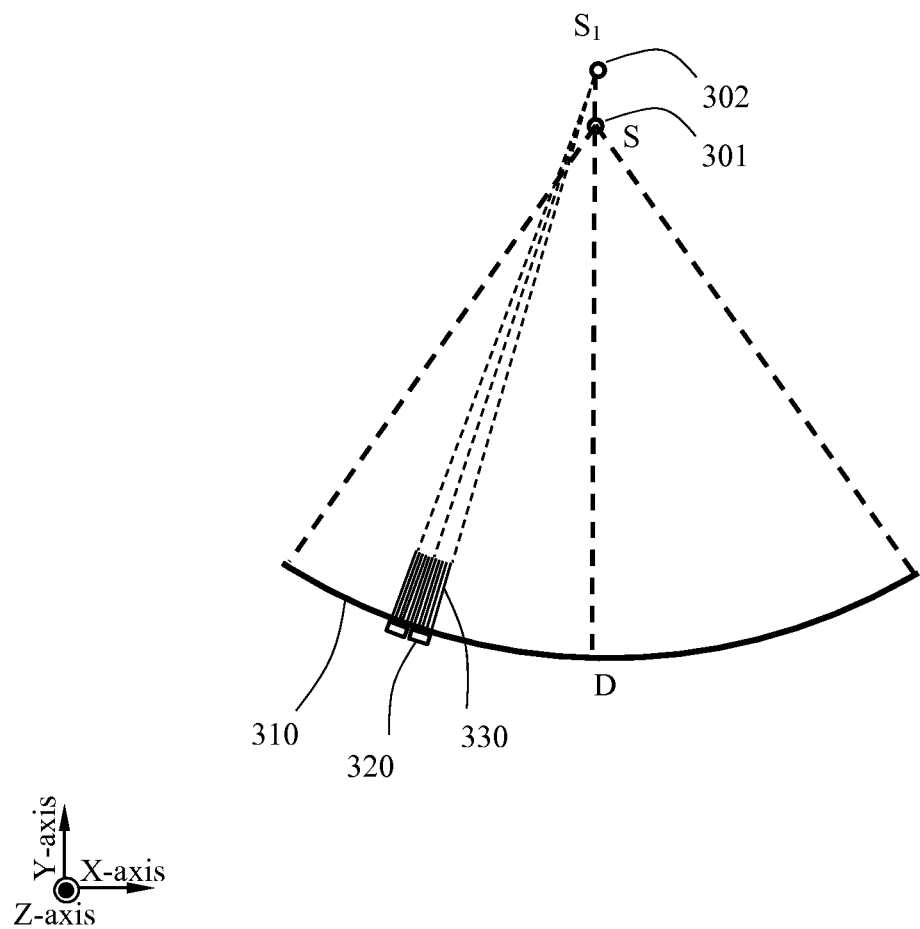
FIG. 3A shows a schematic functional diagram of an Adjustable Photon Detection System (APDS) for multi-slice X-ray CT systems is adjusted to focus on an X-ray source position that the detector modules do not focus on in accordance with one embodiment of the present disclosure.

FIG. 3A shows a schematic functional diagram of an Adjustable Photon Detection System (APDS) for multi-slice X-ray CT systems is adjusted to focus on an X-ray source position $S_1$ 302 that is not at the center S 301 of the arced support structure 310, on which detector modules 320 are mounted, in accordance with one embodiment of the present disclosure. In one embodiment of the present disclosure, the arced support structure 310 is centered at a first position S 301 so that all the detector modules 320 focus on the first position S 301; however, the anti-scatter plates 320 are not aligned to the first position S 301, but are aligned to a second position $S_1$ 302; wherein the X-ray source position is placed at the second position $S_1$ 302; wherein the first position and the second position may be different as shown in FIG. 3A.

Figure 3B:
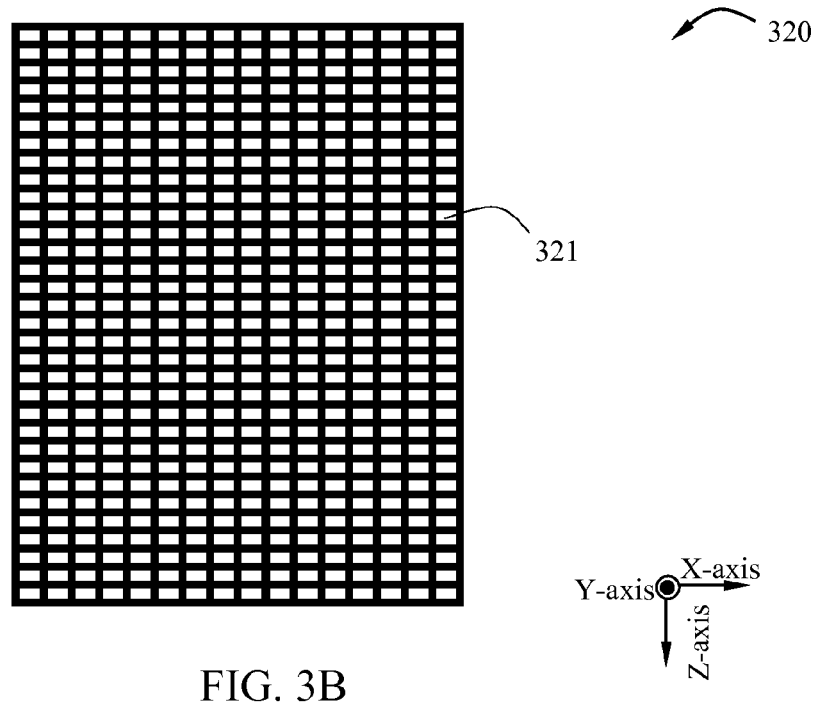
FIG. 3B shows a schematic diagram of a detector module comprising a matrix of detector elements in accordance with one embodiment of the present disclosure.

FIG. 3B shows a schematic diagram of a detector module 320 comprising a matrix of detector elements 321 in accordance with one embodiment of the present disclosure. In accordance with one embodiment of the present disclosure, a detector module 320 is organized in a rectangular matrix of rows and columns of detector elements 321. The column direction is along the Z-axis, and the row direction is along the X-axis. In accordance with one embodiment of the present disclosure, a plurality of detector modules are mounted side by side on a support structure, forming a large cylindrical 2D matrix.

In accordance with one embodiment of the present disclosure, a detector module comprises a scintillator array, a photodiode array to which the scintillator array is bonded. X-ray photons strike on the scintillator array, generating light photons; then the light photons reach the photodiode array, converted to electric charges. In an alternative embodiment, a detector module can also be made of materials, such as CZT, for directly converting X-ray photons to electric charges. In an optional embodiment of the present disclosure, a detector module may also comprise an analog to digital conversion (ADC) card, or an electronic binning card for counting X-ray photons by detecting peaks in electric charges.

In accordance with one embodiment of the present disclosure, each detector element generates an output electric signal or digital signal corresponding to the number, or the energy, of received X-ray photons. The X-ray photons transmitted from the source along a line path to the receiving detector element are called primary X-ray photons; while the X-ray photons originated as a result of the interaction of primary X-ray photons with scanned objects are called scattered X-ray photons, or scatters. The scattered X-ray photons emit to all directions. Therefore, each detector element receives the primary X-ray photons, but also receives scattered X-ray photons. For generating good CT images for diagnosis or other purposes, it is required that each detector element only receive the primary X-ray photons. Anti-scatter plates are used to reduce the scattered X-ray photons from reaching each detector element.

Figure 3C:
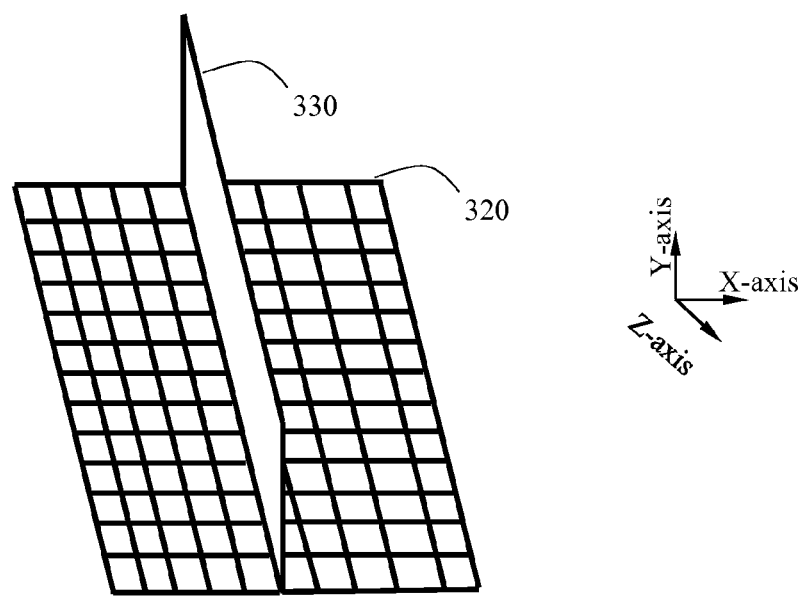
FIG. 3C shows a schematic functional diagram of an anti-scatter plate placed on top of a detector module and placed between two columns of the detector elements in accordance with one embodiment of the present disclosure.

FIG. 3C shows a schematic functional diagram of an anti-scatter plate 330 placed on top of a detector module 320 and between two columns of the detector elements within the detector module 320 in accordance with one embodiment of the present disclosure. Anti-scatter plates are made of high X-ray absorption materials, for example, tungsten. The anti-scatter plates are typically very thin, for example, the thickness is between 100 um to 200 um. The thickness of the anti-scatter plates is based on the gap dimension between neighboring detector elements of the detector module so that the placement of the anti-scatter plates do not block active areas of the detector elements. The height (along the Y-axis) of the anti-scatter plates, for example, 20 mm, is directly related to the amount of scatted X-ray photons that the anti-scatter plates can block and absorb. The higher the anti-scatter plates are, the more scattered X-ray photons are blocked from reaching the active area of the detector elements. Since the anti-scatter plates are placed on top of detector modules, and between any two neighboring columns of detector elements within a detector module and between any two neighboring detector modules, the scattered X-ray photons along the X-axis are mostly blocked; however, the scattered X-ray photons along the Z-axis can still reach the detector elements. To block scattered X-ray photons from both X and Z axes, 2D (two-dimensional) anti-scatter plates can be placed on top of detector modules.

Figures 3D, 3E:
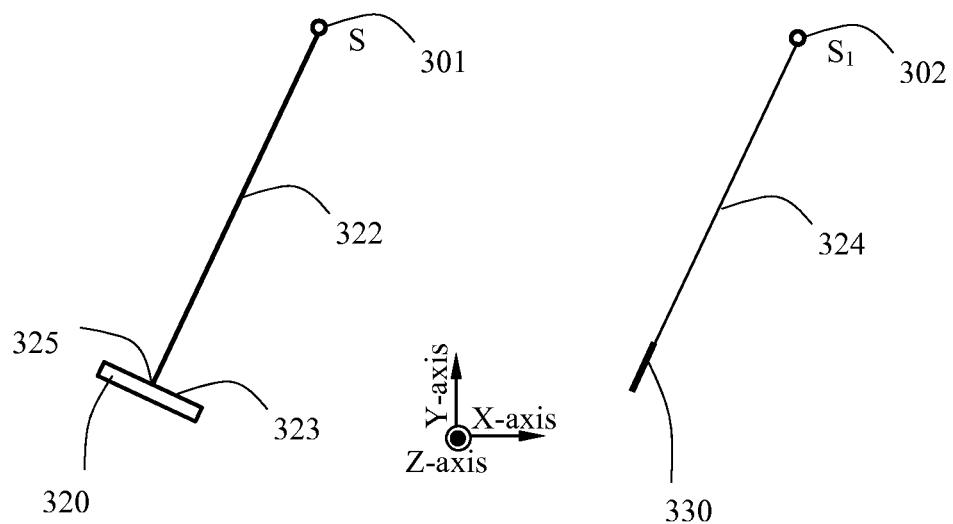
FIG. 3D shows a schematic functional diagram of a detector module focusing on a position in accordance with one embodiment of present disclosure.
FIG. 3E shows a schematic functional diagram of an anti-scatter plate aligned to an X-ray source position in accordance with one embodiment of present disclosure.

FIG. 3D shows a schematic functional diagram of a detector module focusing on a position in accordance with one embodiment of present disclosure. The detector module 320 is mounted in a way such that the X-ray receiving surface 323 of the detector module 320 is perpendicular to the line 322 connecting the X-ray source position S 301 and the center of the detector module 325.

FIG. 3E shows a schematic functional diagram of an anti-scatter plate 330 aligned to a focal spot of an X-ray source $S_1$ 302 in accordance with one embodiment of present disclosure. Each anti-scatter plate 330 is positioned between two columns of detector elements within a detector module 320, in parallel with Z axis; each anti-scatter plate 330 is also aligned to X-ray source position $S_1$ 302 such that the X-ray source position $S_1$ 302 is on the 2D plane 324 extended by the anti-scatter plate 330. Note that the 2D plane 324 is parallel with the Z-axis.

Although the X-ray source position $S_1$ 302 is shown in FIG. 3A further away from the arced support structure 310 than the position S 301, it is understood by those skilled in the art that other positions in vicinity of S 301 can also be chosen as the X-ray source positions and the APDS can be adjusted to focus on these X-ray source positions. For example, $S_1$ 302 can be in vicinity of S 301 within any distance to S 301 that is 10% of the detector focusing distance to the position S 301, which is also the radius of the arced support structure SD as shown in FIG. 3A.

The adjustment of the APDS is to adjust the alignment of the anti-scatter plates 330 (not the anti-scatter plates themselves), and does not change or adjust the arced support structure 310, detector modules 320, or other components of the APDS, such as connection between the detector modules and Analog to Digital Conversion (ADC) boards, motherboards for controlling the ADC boards, fans, heaters, covers, and windows of the APDS. The adjustment of the alignment of the anti-scatter plates 330 is described in details in U.S. patent application Ser. No. 13/589,245, "Configurable data measurement and acquisition systems for multi-slice x-ray computed tomography systems," invented by Zhengrong Ying, filed on Aug. 20, 2012, incorporated herein its entirety by reference. The APDS allows having one design that is adjustable for multi-slice X-ray CT systems of different X-ray source positions with respect to the APDS, lowering the cost for multi-slice X-ray CT systems.

The adjustment of the alignment of the anti-scatter plates 330 is achieved through configuring the slots on the curved anti-scatter toothed metal strips (not shown) that are used to secure and align the anti-scatter plates 330 to different X-ray source positions such as $S_1$ 302 as shown in FIG. 3A. The curved anti-scatter toothed metal strips are made of thin flexible metal strips, such as stainless steel. The curved anti-scatter toothed metal strips are mounted on the arced support structure 310.

In other alternative embodiments of the present disclosure, the support structure may not be an arc shape, for example, a partial regular polygon shape with center at X-ray source position S 301, or other partial non-regular polygon shapes without a center; other variations also include, but not limited to, some or all of the detector modules not focusing on the first position S 301 as shown in FIG. 3A.

Figure 4A:
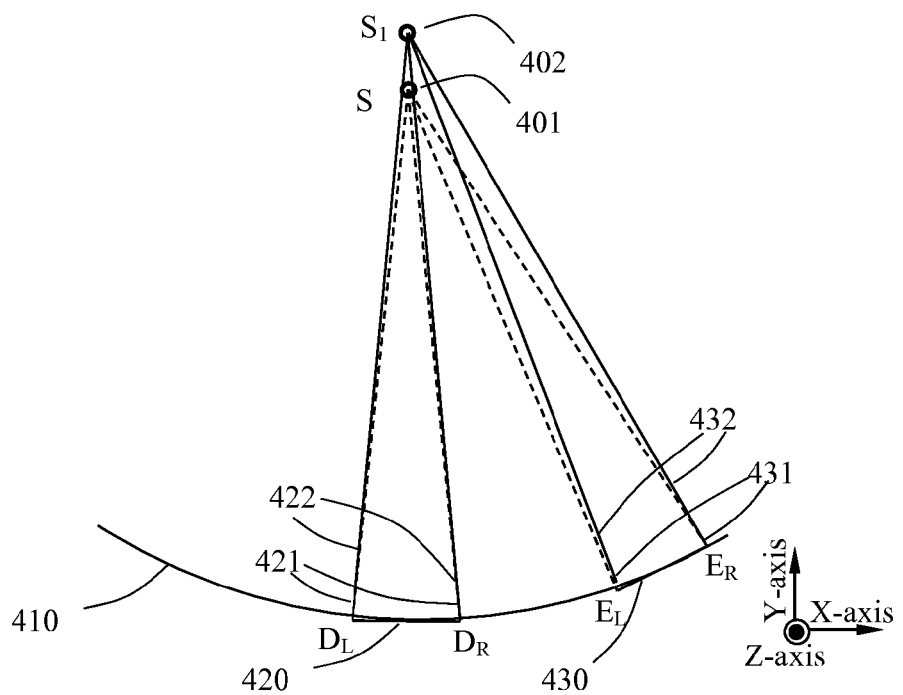
FIG. 4A shows a schematic functional diagram of individual detector elements with anti-scatter plates aligned to different positions in accordance with one embodiment of the present disclosure.

FIG. 4A shows a schematic functional diagram of individual detector elements with anti-scatter plates aligned to different positions in accordance with one embodiment of the present disclosure. The detector element 420 and detector element 430 are mounted on the arced support structure 410. The arced support structure 410 is centered at S 401, and the detector elements 420 and 430 focus on S 401 as well. The anti-scatter plates 421 for the detector element 420 are aligned to S 401, and can be adjusted as indicated by 422 to be aligned to the X-ray source position $S_1$ 402; similarly the anti-scatter plates 431 for the detector element 430 are aligned to S 401, and can be adjusted as indicated by 432 to be aligned to the X-ray source position $S_1$ 402. Note that, in FIG. 4A, the sizes of the detector elements 420 and 430 and the anti-scatter plates 421, 422, 431 and 432 are enlarged not proportional to the arced support structure 410 in order to show the relationship among the arced support structure 410, the detector elements 420 and 430, and the anti-scatter plates 421, 422, 431, and 432 with respect to S 401 and X-ray source position $S_1$ 402.

In accordance with another embodiment of the present disclosure, when the anti-scatter plates are only placed along the column direction (Z-axis), the X-ray source position $S_1$ 402 along the Z-axis is not constrained, in other words, the X-ray source position $S_1$ 402 depicts any possible locations along the Z-axis with the same XY coordinates as $S_1$ 402; similarly, the first position S 401 along the Z-axis is not constrained either.

In accordance with one embodiment of the present disclosure, the detector position of a detector element with respect to a position, for example, S 401 or $S_1$ 402 as shown in FIG. 4A, can be described by a fan angle, a cone angle, and the distance between the position and the center position of the detector element. The fan angle is the angle defined by the line connecting the center of the detector element and the position projected on to the X-Y plane and the line connecting the position and the iso-center; the cone angle is the angle defined by the line connecting the center of the detector element and the position projected on to the Y-Z plane and the line connecting the position and the iso-center. The detector positions of the APDS refer to the detector positions of all the detector elements of the APDS with respect to the position that the detector modules focus on, which is and has been referred to as the first position. The effective detector positions refer to the detector positions of all the detector elements of the APDS with respect to a position (typically an X-ray source position) that is different from the position that the detector modules focus on, which is and has been referred to as the second position.

Figure 4B:
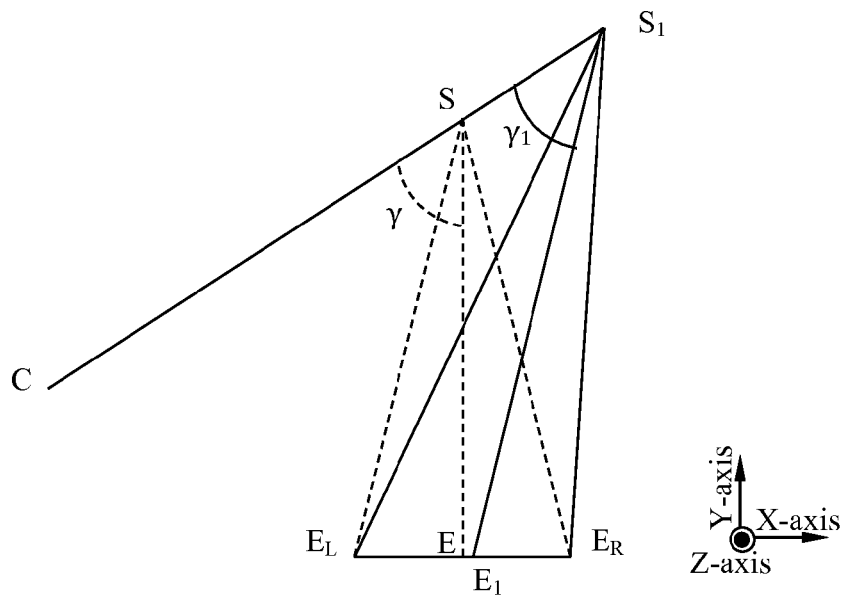
FIG. 4B shows a schematic functional diagram for computing effective fan angles of a detector element with respect to different positions in accordance with one embodiment of the present disclosure.

FIG. 4B shows a schematic functional diagram for computing effective fan angles of a detector element with respect to different positions in accordance with one embodiment of the present disclosure. In this exemplary embodiment of the present disclosure, the first position S that the detector modules focus on, the second position $S_1$ that the anti-scatter plates are aligned to, and the iso-center C are collinear. The detector element $E_L E_R$ focuses on the X-ray source position S, that is, $SE \perp E_L E_R$, and E is the mid-point of $E_L E_R$. The detector pitch $E_L E_R$ is denoted by w. The distance SE is called the nominal focusing distance (same as the radius of the arced support structure 410 in FIG. 4A), denoted by $R_{sd}$. The rotation center of the CT system is indicated by point C. The angle $\angle CSE$ is referred to as a fan angle, denoted by $\gamma$; similarly, in the YZ plane, a cone angle (not shown), denoted by $\tau$, can be defined. The anti-scatter plates are aligned to the X-ray source position $S_1$, which is collinear with C and S for the simplicity of mathematical derivation; computation can be carried out similarly for other positions. The distance $SS_1$ is denoted by $\Delta$. $S_1 E_1$ bisects angle $\angle E_L S_1 E_R$, and the effective fan angle for the X-ray source position $S_1$ for the detector element $E_L E_R$ is denoted by $\gamma_1$. The effective detector pitch $w_1$ is defined as the width of the detector element at distance of $R_{sd}+\Delta$ with the detector element perpendicular to $S_1 E_1$. The following are the steps for computing the effective fan angle $\gamma_1$ and the effective detector pitch $w_1$:

1) Compute $SE_L$ and $SE_R$ $$SE_L = SE_R = \sqrt{R_{sd}^2 + \frac{w^2}{4}} \quad (1.1)$$

2) Compute angles $\angle E_L SE$ and $\angle ESE_R$ $$\angle E_L SE = \angle ESE_R = \tan^{-1}\frac{w}{2R_{sd}} \quad (1.2)$$

3) Compute $S_1 E_L$ $$S_1 E_L = \sqrt{\Delta^2 + R_{sd}^2 + \frac{w^2}{4} + 2\Delta\sqrt{R_{sd}^2 + \frac{w^2}{4}}\cos\left(\gamma - \tan^{-1}\frac{w}{2R_{sd}}\right)} \quad (1.3)$$

4) Compute $S_1 E_R$ $$S_1 E_R = \sqrt{\Delta^2 + R_{sd}^2 + \frac{w^2}{4} + 2\Delta\sqrt{R_{sd}^2 + \frac{w^2}{4}}\cos\left(\gamma + \tan^{-1}\frac{w}{2R_{sd}}\right)} \quad (1.4)$$

5) Compute angle $\angle E_L S_1 E_1$ $$\angle E_L S_1 E_1 = \frac{1}{2}\angle E_L S_1 E_R = \frac{1}{2}\cos^{-1}\frac{S_1 E_L^2 + S_1 E_R^2 - E_L E_R^2}{2 S_1 E_L \cdot S_1 E_R} \quad (1.5)$$

6) Compute angle $\angle SS_1 E_L$ $$\angle SS_1 E_L = \cos^{-1}\frac{\Delta^2 + S_1 E_L^2 - R_{sd}^2 - \frac{w^2}{4}}{2\Delta \cdot S_1 E_L} \quad (1.6)$$

7) Compute the effective fan angle $\gamma_1$ $$\gamma_1 = \angle SS_1 E_L + \angle E_L S_1 E_1 \quad (1.7)$$

8) Compute the effective detector element pitch $w_1$ $$w_1 = 2(R_{sd}+\Delta)\tan \angle E_L S_1 E_1 \quad (1.8)$$

9) Compute $E_L E_1$ $$E_L E_1 = \frac{w \cdot S_1 E_L}{S_1 E_L + S_1 E_R} \quad (1.9)$$

It will be shown below that $E_L E_1 \approx E_L E$, that is, $E_1$ is about the same location as E. With this approximation, the approximated effective fan angle $\gamma'_1$ can be computed by using the sine law for triangle $\Delta SS_1 E$.

$$\gamma'_1 = \tan^{-1}\frac{\sin\gamma}{\cos\gamma + \frac{\Delta}{R_{sd}}} \quad (1.10)$$

The X-ray path length along each detector element also changes with respect to the fan angle $\gamma$. When the X-ray line path perpendicular to the detector element receiving surface, the X-ray path length equals to the detector element depth; when the X-ray line path is not perpendicular to the detector element receiving path, the path length is longer than the detector element thickness. The effective detector thickness, denoted by $d_1$, is defined as the X-ray path length in the detector element, and can be computed from the detector thickness d as follows.

$$d_1 = \frac{d}{\cos(\gamma - \gamma_1)} \quad (1.11)$$

Table 1 shows the computed results of the effective fan angle $\gamma_1$, the difference between the approximated effective fan angle $\gamma'_1$ and the effective fan angle $\gamma_1$, the difference between $E_L E_1$ and $E_L E$, the effective detector pitch $w_1$, and the effective detector thickness $d_1$ with respect to different $\gamma$ and $\Delta$. An example of $R_{sd}$=1000 mm and w=1 mm is used in the computation.

TABLE 1

Computed results of $\gamma_1$, $\gamma'_1$, $d_1$, $E_L E_1$ with respect to $\gamma$ and $\Delta$.

| $\gamma$ (degrees) | $\Delta$ (mm) | $E_L E_1 - E_L E$ (mm) | $\gamma_1$ (degrees) | $\gamma'_1 - \gamma_1$ (degrees) | $(w_1-w)/w$ (%) | $(d_1-d)/d$ (%) |
|---|---|---|---|---|---|---|
| −25 | 50 | −4.8327e−6 | −23.8419 | 2.6478e−7 | 0.4071 | 0.0204 |
| −10 | 50 | −1.9715e−6 | −9.5259 | 1.0765e−7 | 0.0655 | 0.0034 |
| 0 | 50 | 0 | 0 | 0 | 0 | 0 |
| 15 | 50 | 2.9436e−6 | 14.2927 | −1.6086e−7 | 0.1473 | 0.0076 |
| 27 | 50 | 5.1987e−6 | 25.7551 | −2.8502e−7 | 0.4743 | 0.0236 |
| −25 | −50 | 5.7933e−6 | −26.2680 | −3.4751e−7 | −0.5394 | 0.0245 |
| −10 | −50 | 2.4011e−6 | −10.5232 | −1.4468e−7 | −0.0882 | 0.0042 |
| 15 | −50 | −3.5713e−6 | 15.7790 | 2.1496e−7 | −0.1975 | 0.0092 |
| 27 | −50 | −6.2129e−6 | 28.3610 | 3.7236e−7 | −0.6265 | 0.0282 |
| −27 | 100 | −9.5521e−6 | −24.6130 | 5.0165e−7 | 0.8256 | 0.0868 |
| −13 | 100 | −4.6675e−6 | −11.8257 | 2.4359e−7 | 0.1914 | 0.0210 |
| 18 | 100 | 6.4367e−6 | 16.3837 | −3.3650e−7 | 0.3670 | 0.0398 |
| 28 | 100 | 9.8912e−6 | 25.5299 | −5.1978e−7 | 0.8878 | 0.0930 |
| −27 | −100 | 1.3645e−5 | −29.8532 | −8.5614e−7 | −1.4414 | 0.1241 |
| −13 | −100 | 6.8993e−6 | −14.4277 | −4.3771e−7 | −0.3459 | 0.0311 |
| 18 | −100 | −9.4237e−6 | 19.9559 | 5.9599e−7 | −0.6567 | 0.0583 |
| 28 | −100 | −1.4083e−5 | 30.9478 | 8.8269e−7 | −1.5449 | 0.1325 |

In accordance with one embodiment of the present disclosure, effective cone angles can be computed similarly like computing the effective fan angles for the APDS. The effective detector positions with respect to the X-ray source position that the anti-scatter plates are aligned to including effective fan angles, effective cone angles, and the source to detector distance $R_{s1d}$ can be computed as described above.

Figure 5:
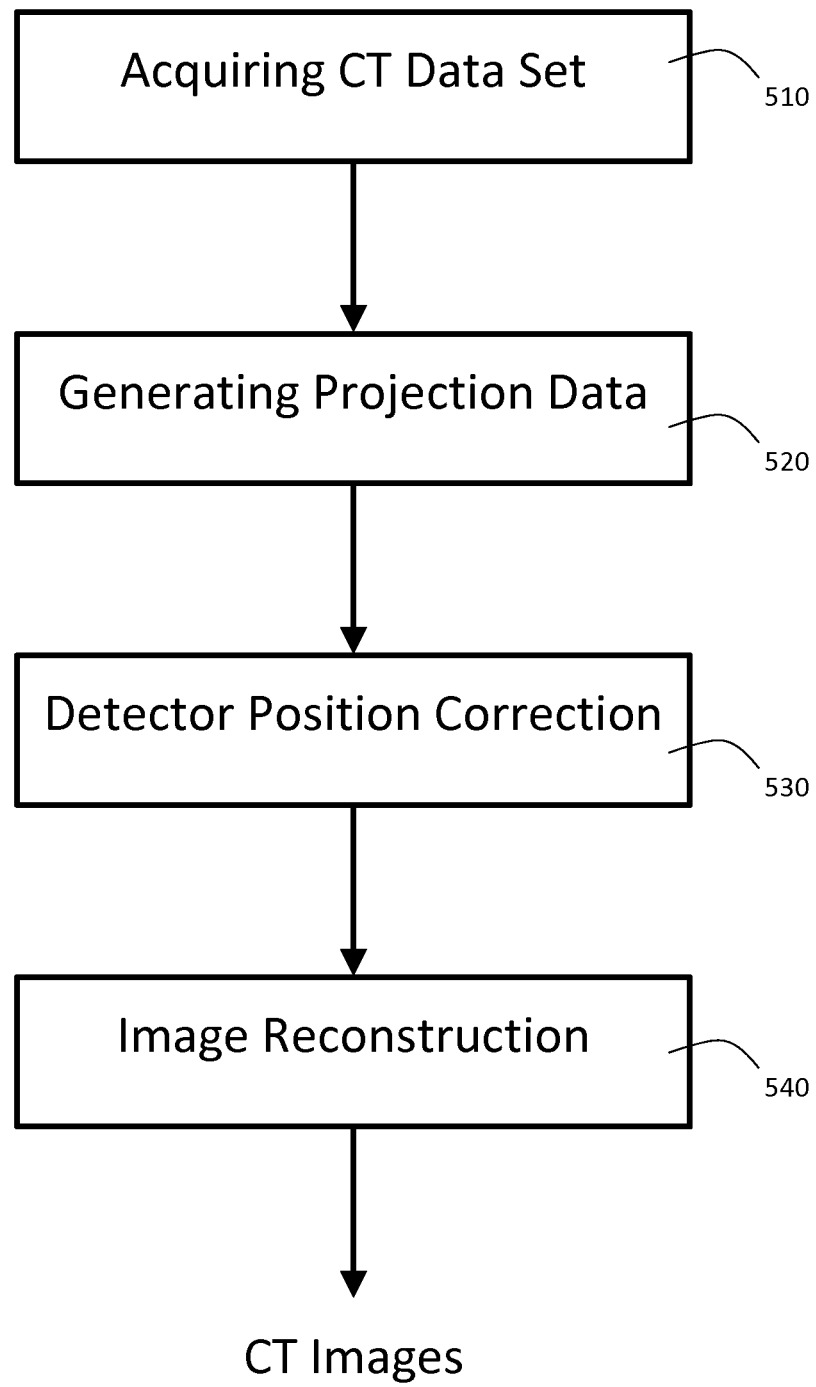
FIG. 5 contains a block diagram which illustrates the logical flow of one embodiment of generating CT images using the APDS with a detector position correction algorithm in accordance with one embodiment of the present disclosure.

FIG. 5 contains a block diagram which illustrates the logical flow of one embodiment of generating CT images using the APDS with a detector position correction algorithm in accordance with one embodiment of the present disclosure. In Step 510, a CT data set is acquired for an object to be imaged. Projection data is then generated from the acquired CT data set in Step 520. A detector position correction algorithm is applied to the generated projection data in Step 530. CT images are then reconstructed by using the detector position corrected projection data in Step 540.

The acquired CT data set is denoted by C(v,r,c), c=0, ..., C−1; r=0, ..., R−1; v=0, ..., V−1; where c is the column index (along X axis) of the detector matrix, r is the row index (along Z axis) of the detector matrix, and v is the view index of the angular positions of the rotating gantry. For APDS, the number of detector rows R, for example, can be 16, 32, 64, 128, 256, 320, or any other numbers. There are usually two types of data acquisition: one is step-and-shoot scanning, and the other is helical scanning. In the step-and-shoot scanning, the patient couch does not move when the CT gantry rotates and the X-ray is on; in the helical scanning, the patient couch moves while the CT gantry rotates and the X-ray is on.

Before acquiring the patient data set C(v,r,c), an air data set has also been collected and saved per mathematical requirement for calculating the attenuation of the X-ray, which is denoted by A(v,r,c). In Step 520, the projection data, denoted by P(v,r,c), can be computed as follows, $$P(v, r, c) = \log \frac{A(v, r, c)}{C(v, r, c)} \quad (1.12)$$

During or before the projection data generation, there might be other algorithms applied to correct for other imperfection of the system hardware or required by physics, such as offset correction, beam hardening correction, detector input response uniformity correction, and others. When the APDS is adjusted to focus on an X-ray source position other than the position on which the detector modules focus, the effective detector pitch and effective detector thickness vary from detector element to detector element. The variations of the effective detector pitch and the effective detector thickness may cause detector elements to have different input responses and sensitivities. However, calibration and corrections algorithms for correcting detector input response uniformity can be applied to correct for such differences; an example of such a calibration and correction algorithm is described in U.S. Pat. No. 4,352,020, "Method and apparatus for examining a subject," invented by Horiba et al, issued on Sep. 28, 1982.

In accordance with one embodiment of the present disclosure, when the APDS is adjusted to be aligned to an X-ray source position other than the position that the detector modules focus on, the effective detector positions with respect to the X-ray source position can be computed in a detector position correction step shown as Step 530 in FIG. 5 to interpolate the non-evenly spaced projection data to evenly spaced projection data for image reconstruction.

For each detector element indexed by (r, c) of the APDS, its fan angle with respect to the position on which the detector modules focus is denoted by $\gamma(r,c)$. In one embodiment of the present disclosure, the detector elements in a same column have same fan angles, thus resulting in $\gamma(r,c)=\gamma(c)$. In yet another embodiment of the present disclosure, the fan angle $\gamma(c)$ is evenly distributed, and $\gamma(c)$ can be expressed as $\gamma(c) = (c-c_o)\cdot\delta$, where $\delta$ is the fan angle increment and $c_o$ is the center detector column position.

Given a fan angle $\gamma(c)$ with respect to position S, an effective fan angle $\gamma_1(c)$ with respect to the source $S_1$ to detector distance $R_{s1d}=R_{sd}+\Delta$ (note that the X-ray source position $S_1$ is different from the position S on which the detector modules focus, and the distance between these two positions is $\Delta$ as discussed previously), then can be computed based on Eq. (1.7) or $\gamma_1(c)=\gamma'_1(c)$ using Eq. (1.10). The projection data P(v,r,c) then can be expressed as a function of effective fan angle as $P(v,r,\gamma_1(c))$. In one embodiment of the present disclosure, the effective fan angle $\gamma_1$ with respect to $R_{s1d}$ is resampled into equally spaced grids to have a form of $\gamma_1(c_1)=(c_1-c_{1o})\cdot\delta_1$, where $c_1$ is the resampled detector column index, $c_{1o}$ is the center detector column position of the resampled detector columns, and $\delta_1$ is the effective fan angle increment. Interpolation methods, for example, linear interpolation method, $4^{th}$ order Lagrange interpolation method, spline interpolation method, can be implemented to compute the evenly spaced projection data $P(v,r,\gamma_1(c_1))$ from non-evenly spaced projection data $P(v,r,\gamma_1(c))$ along the detector row direction.

In accordance with one embodiment of the present disclosure, the interpolation on the projection data on the cone angle direction can also be similarly computed to generate evenly spaced data along the detector column direction. The non-evenly spaced projection data $P(v,\tau_1(r),c)$ can be interpolated to evenly spaced projection data $P(v,\tau_1(r_1),c)$, where the $\tau_1$ is the effective cone angle, and $r_1$ is the resampled detector row index.

In another embodiment of the present disclosure, the source to detector distance can also vary from detector element to detector element, for example, $R_{s1d}(r,c)$ can have different values for each detector element indexed by row index r and column index c.

In accordance with one embodiment of the present disclosure, after interpolation, image reconstruction algorithms, for example, such as filtered backprojection algorithms described in Chapter 3.4.1 of the book "Principles of Computerized Tomographic Imaging" authored by Kak and Slaney published by IEEE Press January 1989 (page 77-86), and "Advanced single-slice rebinning in cone-beam spiral CT," Med. Phys., vol. 27, pp. 754-772, 2000 by M. Kachelriess, S. Schaller, and W. Kalender, can be used to generate CT images.

In an alternative embodiment of the present disclosure, the interpolation step can be omitted if the computed effective fan angle $\gamma_1(c)$ and effective cone angle $\tau_1(r)$ with respect to the source to detector distance $R_{s1d}$ and the projection data $P(v,\tau_1(r),\gamma_1(c))$ are directly used as inputs to image reconstruction algorithms.

In accordance with one embodiment of the present disclosure, an Adjustable Photon Detection System (APDS) for a multi-slice X-ray Computed Tomography (CT) system, wherein said X-ray CT system includes at least one X-ray source, comprises: a plurality of X-ray detector modules for receiving and converting X-ray photons; a support structure for mounting said X-ray detector modules, wherein said detector modules focus on a first position; and, a plurality of anti-scatter plates, placed on top of said detector modules; wherein said anti-scatter plates are aligned to a second position; wherein said second position may be different from said first position.

In accordance with one embodiment of the present disclosure, a multi-slice X-ray Computed Tomography (CT) system for generating CT images for objects to be imaged comprises: a rotatable gantry; an X-ray source mounted on said rotatable gantry for generating X-ray beams to pass through said objects; and an Adjustable Photon Detection System (APDS) mounted on said rotatable gantry to the opposite side of said X-ray source, for receiving said X-ray beams, and for generating a CT data set corresponding to said objects.

In accordance with one embodiment of the present disclosure, a method of and a system for generating CT images comprise: acquiring a CT data set using a multi-slice X-ray CT system comprising an APDS; generating projection data from said CT data set; performing detector position correction on said generated projection data to generate detector position corrected projection data; and, reconstructing CT images using said detector position corrected projection data.

In accordance with one embodiment of the present disclosure, a method of and a system for generating CT images comprise: acquiring a CT data set using a multi-slice X-ray CT system comprising an APDS; generating projection data from said CT data set; calculating effective detector positions; and, reconstructing CT images using said effective detector positions and said generated projection data.

While this disclosure has been particularly shown and described with references to the embodiments thereof, it will be understood by those skilled in the art that various changes in forms and details may be made therein without departing from the spirit and scope of the disclosure as defined by the following claims.

The invention claimed is:

1. An Adjustable Photon Detection System (APDS) for a multi-slice X-ray Computed Tomography (CT) system, wherein said X-ray CT system includes one X-ray source, wherein the center of rotation of said X-ray CT system is iso-center, wherein the direction from said iso-center to the focal spot of said X-ray source is Y-axis, and Z-axis is the axis of rotation, and the direction perpendicular to the Y-axis and Z-axis is X-axis, comprising:
   A. A plurality of X-ray detector modules for receiving and converting X-ray photons; wherein each detector module comprises a plurality of detector elements;
   B. A support structure for mounting said X-ray detector modules, wherein all of said detector modules focus on a first position;
   C. A plurality of anti-scatter plates, placed on top of said detector modules; wherein all of said anti-scatter plates are aligned to a second position; wherein said second position is different from said first position; and,
   D. A plurality of curved anti-scatter toothed metal strips with slots that are configured to align all of said anti-scatter plates to said second position, wherein said curved anti-scatter toothed metal strips are placed on said support structure and are not part of said support structure.

2. The system of claim 1, wherein said support structure is an arced support structure centered at said first position.

3. The system of claim 1, wherein said support structure is a partial regular polygon shaped structure with center located at said first position.

4. The system of claim 1, wherein the distance between said second position and said first position is within 10% of the detector focusing distance to the first position.

5. The system of claim 1, wherein said focal spot of said X-ray source is positioned at said second position, wherein each said detector element of said APDS generates signals corresponding to the X-ray photons only originated from said second position and not from said first position.

6. The system of claim 1, wherein the iso-center about which said multi-slice X-ray CT system rotates, said first position, and said second position are collinear.

7. The system of claim 1, wherein each said detector module includes:

A. A scintillator array for converting X-ray photons to light photons; and,
B. A photodiode array for converting light photons to electric charges; wherein said scintillator array is bonded to photodiode array.

8. The system of claim 1, wherein each said detector module includes:
   A. A direct X-ray conversion array for receiving and directly converting X-ray photons to electric charges; and,
   B. An electronics module for counting the number of received X-ray photons using said converted electric charges.

9. A multi-slice X-ray Computed Tomography (CT) system for generating CT images for objects to be imaged comprising:
   A. A rotatable gantry;
   B. An X-ray source mounted on said rotatable gantry for generating X-ray beams to pass through said objects; and
   C. An Adjustable Photon Detection System (APDS) mounted on said rotatable gantry to the opposite side of said X-ray source, for receiving said X-ray beams, and for generating a CT data set corresponding to said objects; wherein said APDS comprising:
      I. A plurality of X-ray detector modules for receiving and converting X-ray photons; wherein each detector module comprises a plurality of detector elements;
      II. A support structure for mounting said X-ray detector modules, wherein all of said detector modules focus on a first position;
      III. A plurality of anti-scatter plates, placed on top of said detector modules; wherein all of said anti-scatter plates are aligned to a second position; wherein said second position is different from said first position; and,
      IV. A plurality of curved anti-scatter toothed metal strips with slots that are configured to align all of said anti-scatter plates to said second position, wherein said curved anti-scatter toothed metal strips are placed on said support structure and are not part of said support structure;
   wherein the focal spot of said X-ray source is at said second position; wherein the center of rotation of said X-ray CT system is iso-center, wherein the direction from said iso-center to the focal spot of said X-ray source is Y-axis, and Z-axis is the axis of rotation, and the direction perpendicular to the Y-axis and Z-axis is X-axis.

10. The system of claim 9 further includes:
    A. A projection generator constructed and arranged so as to generate projection data from said CT data set;
    B. A corrector constructed and arranged so as to perform detector position correction on said generated projection data to generate detector position corrected projection data; and,
    C. An image reconstructor constructed and arranged so as to reconstruct CT images using said detector position corrected projection data.

11. The system of claim 10, wherein said corrector is constructed and arranged so as to also include computing effective detector positions of said APDS.

12. The system of claim 10, wherein said corrector is constructed and arranged so as to also include computing effective fan angles of said APDS.

13. The system of claim 10, wherein said corrector is constructed and arranged so as to also include computing approximated effective fan angles of said APDS.

14. The system of claim 10, wherein said corrector is constructed and arranged so as to also generate said detector position corrected projection data by interpolating said projection data generated from said projection generator.

15. The system of claim 9 further includes:
    A. A projection generator constructed and arranged so as to generate projection data from said CT data set;
    B. A detector position calculator constructed and arranged so as to compute effective detector positions with respect to a focal spot position of said X-ray source; and,
    C. An image reconstructor constructed and arranged so as to reconstruct CT images using said projection data and said effective detector positions.

16. The system of claim 1, wherein each said detector element along said X-axis corresponds to a first fan angle $\gamma_1$ with respect to said first position and corresponds to a second fan angle $\gamma_2$ with respect to said second position; wherein each said detector element is equi-distant of $R_{sd}$ to said first position and is not equi-distant to said second position; wherein said first fan angle is evenly incremented along said X-axis while said second fan angle is non-evenly incremented along said X-axis.

17. The system of claim 2, wherein said first fan angle $\gamma_1$ and said second fan angle $\gamma_2$ are related approximately by $$\gamma_2 \approx \tan^{-1} \frac{\sin\gamma_1}{\cos\gamma_1 + \frac{\Delta}{R_{sd}}},$$

wherein said first position, said second position, and said iso-center are collinear, and wherein $\Delta$ is the distance between said first position and said second position.

* * * * *